United States Patent [19]

Niggemann et al.

[11] 4,322,237
[45] Mar. 30, 1982

[54] PRESERVING CUT FLOWERS WITH N-(TRIFLUOROMETHYL)-N-(DICHLORO-FLUOROMETHYLSULPHENYL)-AMINOBENZOIC ACIDS

[75] Inventors: Johannes Niggemann, Leverkusen; Engelbert Kühle, Bergisch-Gladbach; Erich Klauke, Odenthal, all of Fed. Rep. of Germany

[73] Assignee: Bayer Aktiengesellschaft, Leverkusen, Fed. Rep. of Germany

[21] Appl. No.: 185,829

[22] Filed: Sep. 10, 1980

[30] Foreign Application Priority Data

Sep. 22, 1979 [DE] Fed. Rep. of Germany ....... 2938414

[51] Int. Cl.³ .............................................. A01N 3/02
[52] U.S. Cl. ..................................................... 71/68
[58] Field of Search ........................................... 71/68

[56] References Cited

FOREIGN PATENT DOCUMENTS 1810580 5/1970 Fed. Rep. of Germany .
2654349 6/1978 Fed. Rep. of Germany .
50-105452 8/1975 Japan .

OTHER PUBLICATIONS

Ger. Offen. 1,908,990, Chem. Abst., vol. 73 (1970) 108730J.

Primary Examiner—Catherine L. Mills
Attorney, Agent, or Firm—Sprung, Felfe, Horn, Lynch & Kramer

[57] ABSTRACT

A method of preserving cut flowers and other parts of plants which have been cut off, comprising placing the flowers or parts of plants in water containing an N-(trifluoromethyl)-N-(dichlorofluoromethylsulphenyl)-aminobenzoic acid, or salt thereof, of the formula

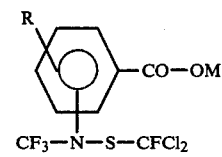

in which M is hydrogen or 1 equivalent of an alkali metal atom or of an alkaline earth metal atom, and R is hydrogen, methyl, methoxy, trifluoro-methyl, chlorine or nitro.

The active material can be employed in the form of a composition also containing water, a carbohydrate and a salt of magnesium, boron or aluminum. It can be held as a dry concentrate on a carrier such as kieselguhr, a natural or synthetic zeolite or alumina.

9 Claims, No Drawings

PRESERVING CUT FLOWERS WITH N-(TRIFLUOROMETHYL)-N-(DICHLOROFLUOROMETHYLSULPHENYL)-AMINOBENZOIC ACIDS

The present invention relates to the use of certain known N-(trifluoromethyl)-N-(dichlorofluoromethylsulphenyl)-aminobenzoic acids and salts thereof for preserving cut flowers and other parts of plants which have been cut off.

It is already known that the life of cut flowers can be increased by adding preserving agents to the water in which the flowers are standing (see, for example, H. Römpp, "Chemie-Lexikon" ("Dictionary of Chemistry"), Franckh'sche Verlagsbuchhandlung Stuttgart (1966), page 733; and J. F. T. Aarts, "Over de houdbaarheid van snijbloemen", Meded. Landouwhogeschool Wageningen/Nederland 57, 1–52 (1957)). However, the preserving action of the agents described is not always satisfactory. This also applies to those agents which consist of a mixture of sugar or a sugar derivative, a pH stabilizer, an organic carboxylic acid with a low molecular weight and a microbicide (in this context, see DT-OS (German Published Specification) No. 1,542,832), or hydrazine sulphate and gibberellic acid (see Swiss Patent Specification No. 432,115). The activity of some components of preservatives does not last long. There are also considerable differences depending on the variety of cut flowers used.

It is furthermore known that N-(trifluoromethyl)-N-(dichlorofluoromethylsulphenyl)-aminobenzoic acid phenylcarboxylic acid esters can be used for preserving cut flowers (see De-OS (German Published Specification) No. 2,654,349. These compounds are not always satisfactory when fairly small amounts are used, and in some cases cause damage to the leaves if used in a fairly high concentration.

The object of the present invention was to develop a preservative for cut flowers which displays a good preserving effect and furthermore enables as many varieties of flowers as possible to be preserved. Only certain combinations of active constituents in preservatives for cut flowers are able to fulfill this requirement, since the microbicidally active component often interacts negatively with the remaining constituents of the preservative.

It has now been found that the N-(trifluoromethyl)-N-(dichlorofluoromethylsulphenyl)-aminobenzoic acids and salts thereof, of the general formula

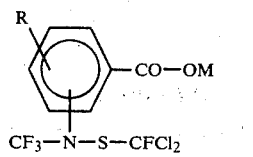

in which
  M represents hydrogen or 1 equivalent of an alkali metal atom or of an alkaline earth metal atom and
  R represents hydrogen, methyl, methoxy, trifluoromethyl, chlorine or nitro,
display preservative properties with cut flowers and parts of plants which have been cut off.

Accordingly, the present invention provides a method of preserving cut flowers and other parts of plants which have been cut off, in which the flowers or parts of the plants are placed in water containing a compound of the formula (I).

The invention also provides cut flowers or other parts of plants whenever preserved by the method of the invention.

Surprisingly, the compounds of the formula (I) which can be used according to the invention and are contained in the preservative as the microbicidal component, in addition to other customary substances, for example sugar derivatives and salts of boron and aluminum, have a number of advantages compared with known preservatives: thus, the life of the cut flowers is considerably increased. The compounds of the formula (I) possess a broad spectrum of action, coupled with a good tolerance, with regard to the various varieties of flowers which are commercially available; no damage to the leaves or blossom is caused. The water in which the flowers stand remains free from microbes. The combinations containing the compounds which can be used according to the invention have an outstanding storage stability. As a result of their good action, the preservatives, for cut flowers, containing the substances of the formula (I) come close to a universal preparation and can replace special preparations (for example for carnations). The use, according to the invention, of the compounds of the formula (I) is thus of interest for horticultural businesses, florists and private households and represents a technical advance.

The formula (I) provides a definition of the N-(trifluoromethyl)-N-(dichlorofluoromethylsulphenyl)-aminobenzoic acids which can be used according to the invention. The use of the following active compounds is of particular interest:

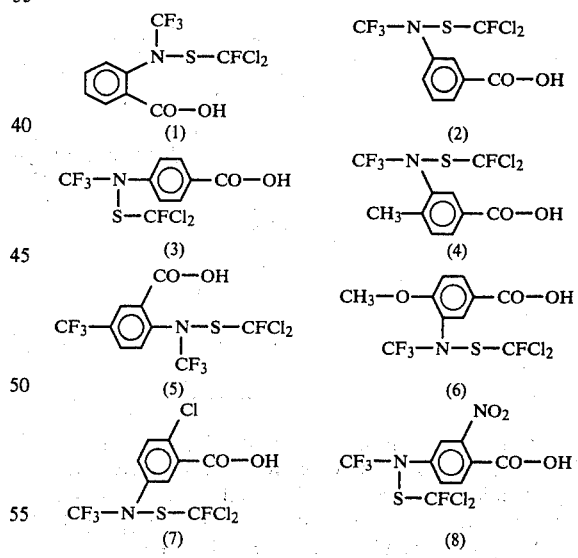

The compounds and their preparation from fluorocarbonyl-N-(trifluoromethylsulphenyl)-anilines and formic acids in the temperature range between 50° and 100° C. are known (see DE-OS (German Published Specification) No. 1,810,580 and the corresponding British Patent Specification No. 1,229,083).

As already stated above, the active compounds which can be used according to the invention can be employed for preserving cut flowers and other parts of plants which have been cut off. They are particularly active against slime-forming bacteria and those pathogenic species of fungus which are frequently to be found in water in flower vases.

The active compounds which can be used according to the invention can be converted into the formulations customary for preservatives. These formulations preferably contain carbohydrates, for example sugar or sugar derivatives, and salts of magnesium, boron or aluminum. In the case of the formulations, a distinction is to be made between liquid formulations and dry concentrates. The liquid formulations contain water and water-soluble organic solvents (for example alcohols, glycols or glycerol) as carriers or diluents. The dry concentrates, which are a formulation form particularly suitable for transportation to distant countries, preferably contain kieselguhr or silicates, aluminas or ground minerals of a natural or synthetic nature as carriers. The formulations are prepared in a known manner, for example by mixing the active compounds with extenders, that is to say liquid solvents or diluents or solid carriers.

The concentration of the active compound in the formulation is from about 0.005 to 1% by weight, preferably about 0.02 to 0.5%, in the case of liquid formulations. In dry concentrates, the active compound concentration is from about 0.05 to 20% by weight, preferably about 0.1 to 10% by weight.

The active compounds to be used according to the invention are preferably used in the form of their formulations or in the use forms prepared therefrom. The concentration of the active compounds in the water in which the cut flowers are standing is usually 0.0005 to 0.5 percent by weight, preferably about 0.001 to 0.2%

The following use examples illustrate the invention. The particular active compounds used according to the present invention are identified by the number (given in brackets) of the formula set forth hereinabove.

EXAMPLE 1

Comparison of the preserving activity of various microbicides according to the invention in the preservative for cut flowers.

Experimental procedure:

The preservative for cut flowers was added to tap water in the concentration indicated. The resulting preserving solution was filled, in equal volumes, into identical vessels. Freshly cut flowers in the same stage of development were placed in these vessels. Each variant, with 10 cut flowers of one variety, was repeated four times. The level of the liquid in the vessels was kept essentially constant by topping up with the corresponding preservative solutions.

Evaluation of the experiment:

The life of the blossom was rated at intervals of time according to the following scale: attractive blossom/blossom withering/withered blossom The following assessment criteria were calculated in accordance with an evaluation method of J. Münch and J. Leinfelder (Die Verlängerung der Haltbarkeit von Schnittblumen (Prolonging the life of cut flowers), annual report 1966/67 of the National Teaching and Research Institute for Horticulture, Weihenstephan, page 92):

(a) The "average life in days" was calculated from the number of days on which the flowers were attractive. The total number of days was divided by the number of flowers per experimental member (variant).

(b) For the "comparison value" (average life in percent), the above-mentioned values were related to the control member (flowers in a commercial preservative for cut flowers = 100).

The basic composition of the preservative for flowers (= "basic PFF") without a microbicide was: 15 g of glucose, 5 g of sucrose, 50 mg of borax ($Na_2B_4O_7 \cdot 10H_2O$), 450 mg of potassium aluminosulphate, alum ($KAl(SO_4)_2 \cdot 12H_2O$) and 250 mg of ammonium aluminosulphate ($NH_3Al(SO_4)_2$).

The experimental results are shown in the following table:

TABLE 1

| Microbicide active compound) in the basic PFF | Dose in mg/l of vase water | Average life in days | Comparison value | Remarks |
|---|---|---|---|---|
| Type of cut flower: Moss roses of the "Marimba" variety ||||  |
| Only tap water | — | 11.5 | — | Solution very turbid as a result of micro-organisms |
| $CF_3-N(-S-CFCl_2)-\text{C}_6\text{H}_4-CO-O-\text{C}_6\text{H}_4-COOH$ (known) | 25 | 12.8 | 100 | Solution brown |
| (2) (according to the invention) | 5 | 15.5 | 121 | Solution clear, |
|  | 15 | 15.5 | 121 | very healthy foliage |
|  | 20 | 14.8 | 116 |  |
| (3) (according to the invention) | 5 | 15.5 | 121 | Solution clear, |
|  | 15 | 15.5 | 121 | very healthy foliage |
|  | 20 | 14.8 | 113 |  |

EXAMPLE 2

Comparisons with a commercial preservative for cut flowers

For the experimental procedure, evaluation of the experiment and composition, see Example 1.

The results can be seen in the following table:

TABLE 2

| Microbicide (active compound) in the basic PFF | Dose in mg/l of vase water | Average life in days | Comparison value |
|---|---|---|---|
| Type of cut flower: Garbera of the "Lila Wunder" variety ||||
| Only tap water | — | 8.0 | — |
| "Substral-Blumenfrisch" | [25ml]** | 8.5 | 100 |

TABLE 2-continued

Type of cut flower: Garbera of the "Lila Wunder" variety

| Microbicide (active compound) in the basic PFF | Dose in mg/l of vase water | Average life in days | Comparison value |
|---|---|---|---|
| (known)* | | | |
| (3) | 2.5 | 13.2 | 155 |
| (according to the invention) | 3.75 | 12.7 | 149 |
| | 5.0 | 11.5 | 135 |

*Product from Messrs. Barnangen-Deutschland G.m.b.H., D-5020 Frechen
**Stated ml of the commercially available liquid formulation required per l of vase water

EXAMPLE 3

Comparison with a commercial preservative for cut flowers.

For the experimental procedure, the evaluation of the experiment and the composition, see Example 1.

The results can be seen from the following table:

TABLE 3

Type of cut flower: Moss rose of the "Garnette" variety

| Microbicide (active compound) in the basic PFF | Dose in mg/l of vase water | Average life in days | Comparison value | Remarks |
|---|---|---|---|---|
| Only tap water | — | 11.5 | — | Solution very turbid as a result of micro-organisms |
| (R) "Substral-Blumentfrisch" (known)* | [25ml]* | 11 | 100 | Solution turbid |
| (3) (according to the invention) | 2.5 | 13.9 | 126 | Solution somewhat turbid |
| | 3.75 | 14.6 | 133 | Solution somewhat turbid |
| | 5.0 | 14.1 | 128 | Solution clear |

*See the information given below Table 2

EXAMPLE 4

Comparison with a commercial preservative for cut flowers.

For the experimental procedure, the evaluation of the experiment and the composition, see Example 1.

The results can be seen from the following table:

TABLE 4

Type of cut flower: True carnation of the "Nora" variety

| Microbicide (active compound) in the basic PFF | Dose in mg/l of vase water | Average life in days | Comparison value | Remarks |
|---|---|---|---|---|
| Only tap water | — | 8.0 | — | Solution very turbid as a result of micro-organisms |
| (R) "Chrysal" (known)* | [12.5g]** | 8.5 | 100 | Solution somewhat turbid |
| (3) (according to the invention) | 2.5 | 13.0 | 153 | Solution somewhat turbid |
| | 3.75 | 12.2 | 144 | Solution somewhat turbid |
| | 5.0 | 13.3 | 157 | Solution clear |

*Manufacturer: Messrs. Bendien, Naarden/Holland
**Stated g of the commercially available formulation required per l of vase water

EXAMPLE 5

Comparison with a commercial preservative for cut flowers.

For the experimental procedure, the evaluation of the experiment and the composition, see Example 1.

The results can be seen from the following table:

TABLE 5

Type of cut flower: Gabera of the "Yamee" variety

| Microbicide (active compound) in the basic PFF | Dose in mg/l of vase water | Average life in days | Comparison value | Remarks |
|---|---|---|---|---|
| Only tap water | — | 8.0 | — | Solution very turbid as a result of micro-organisms |
| (R) "Chrysal" (known)* | [12.5g]* | 11.7 | 100 | Solution clear |
| (3) (according to the invention) | 2.5 | 12.5 | 107 | Solution somewhat turbid |
| | 3.75 | 13.5 | 115 | Solution clear |
| | 5.0 | 15.5 | 132 | Solution clear |

*In this context, see the information given for Example 4

It will be appreciated that the instant specification and examples are set forth by way of illustration and not limitation, and that various modifications and changes may be made without departing from the spirit and scope of the present invention.

What is claimed is:

1. In the preservation of cut flowers and other parts of plants which have been cut off by placing the flowers or parts of plants in water containing an aminobenzoic acid derivative as a preservative, the improvement which comprises employing as said preservative an N-(trifluoromethyl)-N-(dichlorofluoromethyl-sulphenyl)-aminobenzoic acid, or salt thereof, of the formula

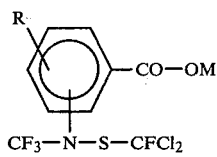

in which
   M is hydrogen or 1 equivalent of an alkali metal atom or of an alkaline earth metal atom, and
   R is hydrogen, methyl, methoxy, trifluoro-methyl, chlorine or nitro.

2. A method according to claim 1, wherein the concentration of the acid or salt in the water is between about 0.0005 and 0.5 percent by weight.

3. A method according to claim 1, wherein the concentration of the acid or salt in the water is between about 0.001 and 0.2 percent by weight.

4. A method according to claim 1, wherein the water also contains a carbohydrate and a salt of magnesium, boron or aluminum.

5. A method according to claim 1, wherein the compound is selected from the group consisting of

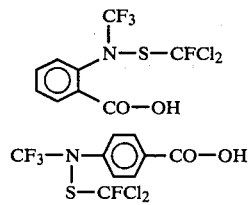

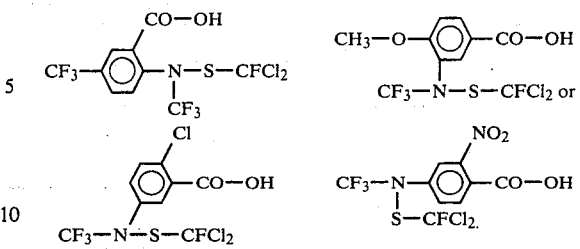

6. A method according to claim 5, wherein the concentration of the acid or salt in the water is between about 0.001 and 0.2 percent by weight and the water also contains a carbohydrate and a salt of magnesium, boron or aluminum.

7. A method according to claim 1, wherein the compound is

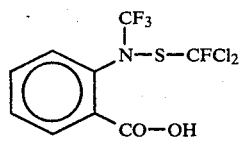

8. A method according to claim 1, wherein the compound is

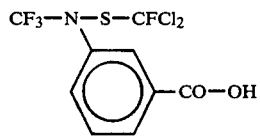

9. A method according to claim 1, wherein the compound is

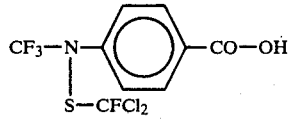

* * * * *